United States Patent
Bloom et al.

(10) Patent No.: US 9,422,258 B2
(45) Date of Patent: Aug. 23, 2016

(54) REDUCTION OF HMF ETHERS WITH METAL CATALYST

(71) Applicant: ARCHER DANIELS MIDLAND COMPANY, Decatur, IL (US)

(72) Inventors: Paul Bloom, Forsyth, IL (US); Alexandra Sanborn, Lincoln, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/215,157

(22) Filed: Mar. 17, 2014

(65) Prior Publication Data

US 2014/0239230 A1  Aug. 28, 2014

Related U.S. Application Data

(60) Division of application No. 13/096,348, filed on Apr. 28, 2011, now Pat. No. 8,709,286, which is a continuation of application No. PCT/US2009/062778, filed on Oct. 30, 2009.

(60) Provisional application No. 61/109,634, filed on Oct. 30, 2008.

(51) Int. Cl.
| | | |
|---|---|---|
| *C07D 307/54* | (2006.01) | |
| *C07D 307/16* | (2006.01) | |
| *C07C 41/26* | (2006.01) | |
| *C07C 43/13* | (2006.01) | |
| *C07D 307/12* | (2006.01) | |
| *C07D 307/44* | (2006.01) | |
| *C08K 5/06* | (2006.01) | |

(52) U.S. Cl.
CPC .............. *C07D 307/54* (2013.01); *C07C 41/26* (2013.01); *C07C 43/13* (2013.01); *C07D 307/12* (2013.01); *C07D 307/16* (2013.01); *C07D 307/44* (2013.01); *C08K 5/06* (2013.01)

(58) Field of Classification Search
CPC ........................... C07D 307/54; C07D 307/16
USPC ......................................................... 252/364
See application file for complete search history.

(56) References Cited

U.S. PATENT DOCUMENTS

| | | | | | |
|---|---|---|---|---|---|
| 4,025,558 | A | * | 5/1977 | Lednicer ................. | C07C 45/44 540/543 |
| 5,405,865 | A | * | 4/1995 | Benoit ................... | A01N 43/08 514/438 |
| 6,008,418 | A | * | 12/1999 | Baur ..................... | C07C 29/149 568/852 |
| 7,411,078 | B2 | * | 8/2008 | Miura ................... | C07D 307/44 549/484 |
| 7,579,490 | B2 | * | 8/2009 | Sanborn ................ | C07C 51/245 549/502 |
| 2006/0128844 | A1 | * | 6/2006 | Sanborn ................ | C07C 51/245 524/111 |
| 2007/0287845 | A1 | * | 12/2007 | Lilga .................... | C07D 307/46 549/503 |
| 2009/0048471 | A1 | * | 2/2009 | Ii .......................... | C07C 29/149 568/884 |
| 2011/0082304 | A1 | * | 4/2011 | Gruter ...................... | C10L 1/02 549/488 |
| 2013/0345449 | A1 | * | 12/2013 | Partin .................. | C07D 307/68 549/485 |

FOREIGN PATENT DOCUMENTS

| | | | | | |
|---|---|---|---|---|---|
| GB | | 798318 | A | * 7/1958 | |
| WO | WO 2010062689 | A2 | * 6/2010 | ............. C07C 41/26 |

OTHER PUBLICATIONS

Lewkowski et al. Acylation of THF. 2001.*

* cited by examiner

*Primary Examiner* — Nicole M Buie-Hatcher
*Assistant Examiner* — M. Reza Asdjodi
(74) *Attorney, Agent, or Firm* — Alexandra Sanborn

(57) ABSTRACT

Methods of making reduced derivatives of hydroxymethyl furfural using metal catalysts are described. The derivatives may have tetrahydrofuran or furan nucleus with alkoxymethyl ether or ester moieties on the 5' carbon and methanol on the 2' carbon. Suitable metal catalyst include Raney nickel, a nickel catalyst with a zirconium promoter, a chromite catalyst with a barium, a palladium catalyst, such as palladium on carbon, or a ruthenium catalyst. Also provided are a new class of compounds, which are n-alkoxy hexane diols (i.e., 1,2 or 1,5 hexane diol ethers) and methods of making the same by reduction of furan or tetrahydrofuran derivatives.

10 Claims, 6 Drawing Sheets

REDUCTION OF HMF ETHERS WITH METAL CATALYST

PRIORITY CLAIM

This application is a divisional application of prior, co-pending U.S. application Ser. No. 13/096,348 filed Apr. 28, 2011, and claims priority to PCT Application Serial No. PCT/US2009/062778 filed Oct. 30, 2009, which itself claims the benefit under 35 U.S.C. §119(e) of U.S. Provisional Application Ser. No. 61/109,634, filed Oct. 30, 2008, which are incorporated herein by reference in their entirety.

TECHNICAL FIELD

This disclosure relates to methods of reducing hydroxymethylfurfural derivatives. More particularly, this disclosure relates to methods of reducing hydroxymethylfurfural ethers and hydroxymethylfurfural esters with hydrogen in the presence of a metal catalyst to produce 5-(alkoxymethyl)-tetrahydrofuran-2-methanol or 5-alkoxymethyl)-furan-2-methanol derivatives and purification thereof. In addition, the disclosure relates to n-alkoxy hexane diol compounds, which are derivative compounds useful for replacement of petroleum based carbitol compounds that can be made from the reduced hydroxymethylfurfural ethers made according to the methods of the present disclosure.

BACKGROUND

The use of naturally derived material as starting materials and intermediates for commercial products is a growing industry. For example, a great deal of research is being conducted to convert natural products into fuels as a cleaner alternative to fossil-fuel based energy sources. Agricultural raw materials such as starch, cellulose, sucrose or inulin are inexpensive and renewable starting materials for the manufacture of hexoses, such as glucose and fructose. Fructose, an abundant compound derived from natural products such as corn, may be converted to other materials, such as hydroxymethylfurfural, or HMF, and its related ethers.

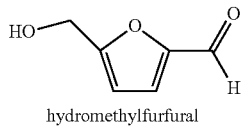

hydromethylfurfural

One desirable derivative of HMF ethers is a partial reduction product which converts the aldehyde moiety of HMF to an alcohol. Although there is no known method for the reduction of HMF ethers, one method of reducing aldehydes to alcohols is described by Eller et al. in U.S. Pat. No. 6,350,923. This method uses a metal catalyst, such as nickel, cobalt or copper, reacted with the aldehydes at elevated temperatures and pressures. However, the method does not mention the ability of the catalyst to reduce a C=C bond.

Methods used to synthesize products that are similar to HMF ethers are also inadequate in terms of yield and use of undesirable reactants. For example, a method of synthesizing an equivalent of an HMF ether derivative without the use of HMF as a starting material is described by Pevzner et al. (*Zhurnal Organicheskoi Khimii* (1987), 23(6), 1292-4). In this method, an alkyloxymethylfuran is reacted with paraformaldehyde at 70-80° C. for 3 hours to give 2-hydroxymethyl-5-alkyloxymethylfuran. However, the yield was poor 55%, and in addition, the reaction requires the use of paraformaldehyde, a known irritant to the respiratory system and skin.

The product guide for G-693 nickel on kieselguhr with zirconium promoter catalyst (Sud Chemie) lists the catalyst as useful for reduction of terpenes, which contain C=C bonds. However, as is well known in the art, the furan ring in HMF, which contains two conjugated C=C bonds, is much more difficult to reduce than non-conjugated C=C bonds. Furthermore, the guide does not mention the ability of the catalyst to reduce aldehydes.

The present disclosure addresses the shortfalls of the prior art and provides methods for reducing the aldehyde and/or C=C bond of HMF ethers to the resulting alcohol and C—C bond, respectively, at high yields.

SUMMARY OF THE DISCLOSURE

In one aspect, the present disclosure provides methods of reducing HMF ethers and esters with hydrogen in the presence of a metal catalyst to produce 5' alkoxy substituted furans or tetrahydrofurans or, 5' acylmethyl substituted furans or tetrahydrofurans in the case of esters. Also proved are derivatives of such compounds and uses for such compounds. Also provided are bio-based compositions comprising such compounds as determined by ASTM International Radioisotope Standard Method D 6866.

In another aspect the present disclosure provides for derivative compositions that can be made from the hydrogenated HMF ethers and esters and methods of making the same. In certain embodiments the derivative compositions, like the starting compositions, are useful as solvents, cross-linking and grafting reagent and the disclosure provides for ways of using said compositions as bio-based renewable substitutes for petroleum based compositions, including in certain exemplary embodiments, substitutes for petroleum based carbitol solvents.

Embodiments of methods of making the forgoing compounds include, contacting a hydroxymethyl furfural 5' R ether or ester, where R is an alkyl group of 1 to 5 carbons, with a metal catalyst capable of reducing the furfural compound in the presence of hydrogen. In one embodiment, the catalyst is a nickel catalyst such as Raney Nickel. In another embodiment the catalyst is a nickel catalyst with a zirconium promoter exemplified by the product G-69B available from Sud Chemie. In yet another embodiment the catalyst is can be a chromite catalyst with a barium promoter exemplified by the product G-22 also available from Sud Chemie. In yet another embodiment the catalyst can be a palladium catalyst, such as palladium on carbon exemplified by the catalyst Pd/C. In yet another embodiment the catalyst can be a ruthenium catalyst. In typical embodiments, the hydrogenation is conducted, at a temperature, a pressure and a time sufficient to convert at least 40% of the 5' alkoxy hydroxymethyl furfural to the (5' alkoxy)-furan or tetrahydrofuran compositions mentioned above. In other embodiments at least 80% of the 5' alkoxy hydroxymethyl furfural is converted to the 5' alkoxy furan or tetrahydrofuran Another aspect is use of the forgoing 5'-alkoxy or 5'acylmethyl-furan or tetrahydrofurans and/or derivatives thereof as bio-based replacements for petroleum based solvents.

Another aspect is a new class of n-alkoxy hexane diols of the formula:

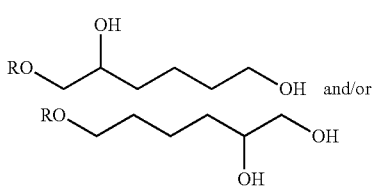

wherein R may be is an alkyl group of 1 to 24, or more typically 1-5, carbons, which are made by further contacting the foregoing (5-alkoxymethyl)-furan-2-methanol or (5-alkoxymethyl)-tetrahydrofuran-2-methanol compounds with hydrogenation catalyst, preferably a Ni catalyst, for a time sufficient to open the ring of the furan or tetrahydrofuran derivative.

These alkoxy hexane diol compounds are useful as solvents that can substitute for petroleum based glycol ether solvents.

DETAILED DESCRIPTION OF THE DISCLOSURE

Figure 1:
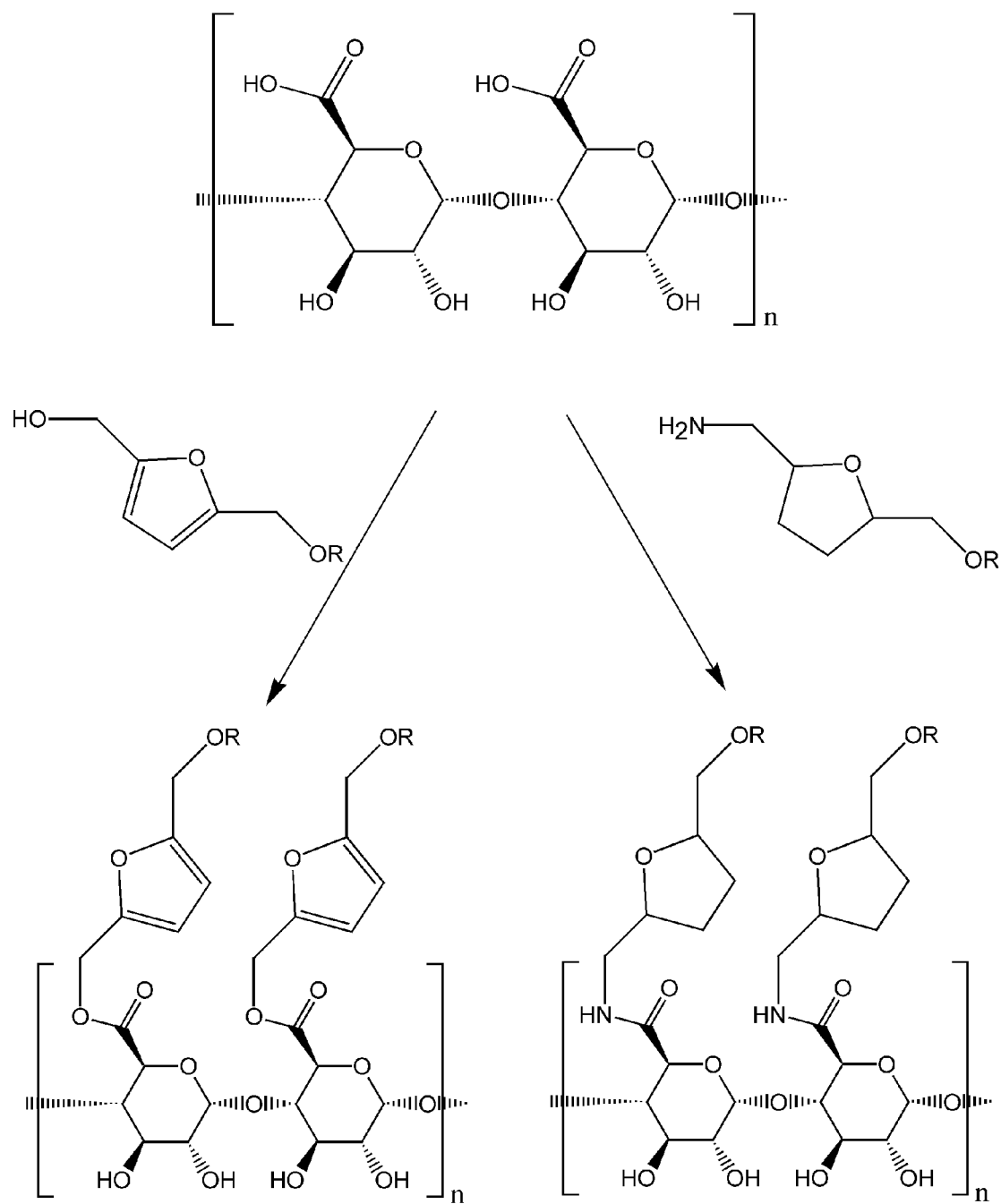
FIG. 1 shows aminated alkoxy tetrahydrofuran or furan starch derivatives made possible by certain embodiments of the invention.

The present disclosure provides methods for reducing hydroxymethylfurfural (HMF) ethers and esters and provides for derivatives that can be made therefrom. It also provides for a novel class of such compounds defined at least in part because these compounds meet the standards for industrial chemicals derived from renewable resources rather than petroleum based resources. The bio-based compounds of the present invention can be used as substitutes for similar or identical compounds derived from petroleum based resources.

There are known methods for determining the bio-based content, therefore determining whether organic compositions are obtained from renewable resources. These methods require the measurement of variations in isotopic abundance between bio-based products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-based products compared to petroleum products. The bio-based content of a product may be verified by ASTM International Radioisotope Standard Method D 6866. ASTM International Radioisotope Standard Method D 6866 determines bio-based content of a material based on the amount of bio-based carbon in the material or product as a percent of the weight (mass) of the total organic carbon in the material or product. Bio-derived and bio-based products will have a carbon isotope ratio characteristic of a biologically derived composition.

The class of compounds provided herein are therefore distinguishable from petroleum based compounds of similar or identical structure, in that in all embodiments, the compounds provided herein have a bio-based content of at least 37.5% when measured according to ASTM International Radioisotope Standard Method D 6866. This minimum bio based content is achieved by recognizing that the entire 6 carbons originating from the hydroxymethyl furfural nucleus of the compounds originate from a carbohydrate, typically fructose, which is derived from plants. In some embodiments the bio based content is 100% according the ASTM standard. Compounds having a bio based anywhere between 37.5% and 100% can be made by appropriate selection of another bio-based reagent for combining with the HMF nucleus. For example, if the starting compound is a $C_5$ alkoxy ether of HMF that was made by addition of a isoamyl alcohol obtained from a petroleum source with the HMF from a biological source, the resulting compound of the present invention would have a bio-based content of 6/11 or 54.5%. If however, the isoamyl residue was also obtained from a bio-based renewable resource compound such as isoamyl alcohol obtained by distillation of fusel oils made during a fermentation process where the carbons originate from sugar, then the compounds of the present invention would have a bio based content of 100%.

Turning now to methods of making, generally these methods include the steps of combining a hydroxymethylfurfural ether or ester with a solvent in a reaction vessel, followed by addition of a metal catalyst. The reaction vessel is then charged with hydrogen gas. The reaction mixture is then stirred at elevated temperature and pressure, cooled and filtered to remove the catalyst. The solvent is then removed to yield the reduced product.

So there is no ambiguity, the terms "hydroxymethylfurfural ether," "furfural ether," and "HMF ether" are used interchangeably herein and refer to molecules that are more technically designated R-5' alkoxy methyl furfural ethers having the general structure:

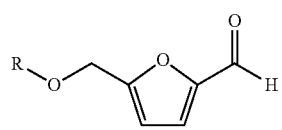

The terms "HMF ester," "furfural ester," and "hydroxymethylfurfural ester" are used interchangeably herein and refer to molecules that are more technically designated R-5' acyl methyl furfural esters having the general structure:

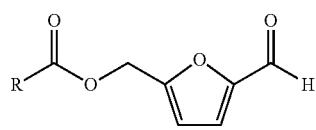

In each case R is an alkyl group that may be either straight chained or branched, having from 1 to 24 carbon atoms, and may also contain oxygen, nitrogen or sulfur. Some preferred alkyl groups are the $C_1$ to $C_5$ alkyl moieties such as methyl, ethyl, n-propyl, i-propyl, i-butyl, n-butyl, i-amyl and n-amyl. These alkyl substituted HMF compounds can be derived from natural bio-based sources. For example, methyl substituted HMF ethers can be synthesized from methanol derived from biomass gasification. Alternatively, the $C_1$-$C_5$ alkyl groups can be obtained from ethanol and fusel oil alcohols. Fusel oil is a by-product of carbohydrate fermentations whose main components are isopentyl alcohol and 2-methyl-1-butanol, and to a lesser degree contains isobutyl alcohol, n-propyl alcohol, and small amounts of other alcohols, esters and aldehydes. In addition, n-butanol may be derived from the fermentation of acetone/ethanol or from the catalytic condensation of ethanol.

These methods utilize metal as the catalyst for the reaction. Some preferred metal catalysts are nickel and copper. One more preferred catalyst is G-69B, a powdered catalyst containing 62% nickel on Kieselguhr and having a zirconium promoter, available from Sud-chemie Corp. (Louisville, Ky.). The average particle size of G-69B is 10-14 microns, 43% nickel by weight. Another preferred catalyst is G22/2 also available from Sud-chemie Corp. G22/2 is a barium promoted copper chromite catalyst, 39% Cu and 24% Cr. Another preferred catalyst is G-96B also available from Sud-Chemie Corp. G-96B is a nickel on silica/alumina, 66% nickel by weight, particle size 6-8 microns. One more preferred catalyst G-49B available from Sud-Chemie Corp. Particle size is 7-11 microns and 55% nickel by weight. Another preferred catalyst is palladium on carbon, exemplified by the catalysts Pd/C.

The amount of catalyst used in the reaction is preferably sufficient to allow for efficient reduction of the starting material to the desired product. Too little catalyst results in the reaction proceeding at a slow rate and may result in degradation of the starting material and products from elongated reaction times. The use of too much catalyst may result in increased costs of both catalyst and disposal of the catalyst. Generally, the preferred amount of catalyst used in the reaction is from 0.5 to 15 wt/wtl %, of starting material, more preferably from about 5 to 14 wt/wtl % of starting material and most preferably about 8 to 12 wt/wt % of starting material. The methods can use either purified or partially purified starting materials and result in different desired products as described in more detail hereafter. Therefore, to be clear, the reference to any amount, or an amount relative to "starting material" means the total amount of fufural compounds in the reaction mixture, including HMF, HMF ether or HMF esters, even though the reaction mixture may contain other compounds not pertinent to the reaction, most typically levulinic acid.

The metal catalyst may be supported with a support material. Suitable support materials include silicic acid, silica gel or siliceous earth, or diatomaceous earth. One preferred diatomaceous earth, kieselguhr, is a soft, chalk-like sedimentary rock that is easily crumbled into a fine white to off-white powder. This powder has an abrasive feel, similar to pumice powder, and is very light, due to its high porosity. The typical chemical composition of diatomaceous earth is 86% silica, 5% sodium, 3% magnesium and 2% iron. Kieselguhr is a naturally occurring material which consists of fossilized remains of diatoms, a type of hard-shelled algae.

In different embodiments, reduction, or hydrogenation of HMF ethers, may involve complete hydrogenation or partial hydrogenation, as depicted by the following diagram, which depicts the partial and complete reduction products of HMF ethers obtained by use of the methods herein.

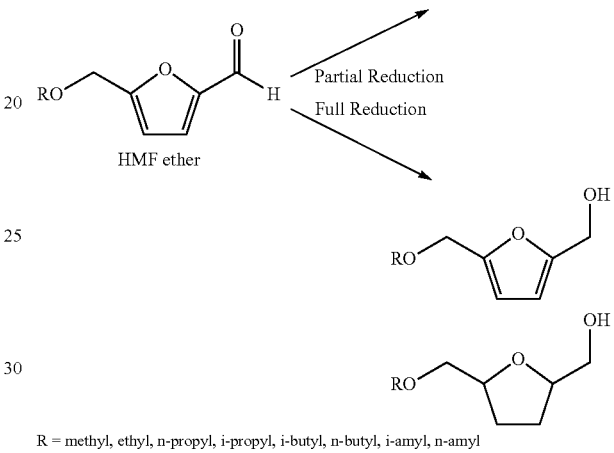

R = methyl, ethyl, n-propyl, i-propyl, i-butyl, n-butyl, i-amyl, n-amyl

As used herein, complete hydrogenation of the HMF ether results in reduction of the aldehyde moiety to an alcohol group and reduction of the furan ring to tetrahydrofuran derivative forming a (5-alkoxymethyl)-tetrahydrofuran-2-methanol compound of the structure:

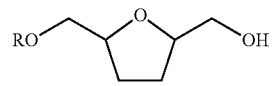

The conditions for complete reduction of the HMF ether generally require the use of purified HMF starting material, more active catalyst, and elevated temperatures and pressures. As used herein "purified" means the percentage of the HMF ether as fraction of the total furfural components in the reaction mixture is at leas 40%. Example reaction conditions for complete reduction of HMF ethers are shown in Table 1:

TABLE 1

| HMF ether | Catalyst wt/wt % catalyst to furfurals | % HMF ether Purity | Temperature - time | pressure (psi) | % converson* |
|---|---|---|---|---|---|
| Ethyl HMF | 12% G 69B | >80% | 15° C. - 4 h then 200° C. - 9.5 h | 1500 | >98% |
| Ethyl HMF | 12% G 69B | >80% | 200° C. - 14 h | 1350 | >98% |
| Ethyl HMF | 12% G 69B | >80% | 250° C. - 11.5 h | 1150 | >98% |
| Butyl HMF | 5% G 69B | >95% | 170° C. - 1 h | 1000 | >98% |
| Butyl HMF | 5% G 69B | >95% | 200° C. - 1 h | 1000 | >98% |
| Butyl HMF | 1% G 69B | 56% | 200° C. - 5 h | 1000 | >98% |

TABLE 1-continued

| HMF ether | Catalyst wt/wt % catalyst to furfurals | % HMF ether Purity | Temperature - time | pressure (psi) | % converson* |
|---|---|---|---|---|---|
| Butyl HMF | 7% Raney Ni | 42% | 200° C. - 5 h | 1000 | >98% |
| Butyl HMF | 7% Raney Ni | 42% | 200° C. - 5 h | 1200 | >98% |
| Isoamyl HMF | 10% G 69B | >80% | 200° C. - 1 h | 1400 | >98% |

*% conversion means percent of HMF ether transformed - not necessarily converted to the fully reduced species - the percentage of which was not quantified.

These conditions indicate that in particular, these Nickel based catalyst are most active and therefore most suitable for complete hydrogenation of various HMF ethers to their 5' alkoxy tetrahydrofuran derivatives and that complete hydrogenation can occur when the purity of the HMF ether is greater than 40%

In other embodiments of the method as described herein, partial reduction of the HMF ether involves conversion of the aldehyde to the alcohol group without hydrogenation of the double bonds in the furan ring, resulting in a (5-alkoxymethyl)-furan-2-methanol compounds to form a compound of the structure:

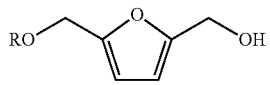

In certain practices for partial hydrogenation purified samples of the HMF ether may be used, and reaction conditions are conducted under less pressure, and for less time. Table 2 summarizes reaction conditions suitable for partial reduction of purified butoxy methyl furfural (BMF) as an exemplary reactant:

TABLE 2

| catalyst | temp C. | pressure (psi) | time (h) | BMF (g/kg) | partially reduced BMF (g/kg) | Conversion (%) |
|---|---|---|---|---|---|---|
| 1% G69B | 200 | 1000 | 2 | 559.6 | na | 75.3 |
| 1% G69B |  |  |  | 147.43 | na | na |
| 6% G69B | 200 | 800 | 2 | 700 | na | na |
| 10% G22/2 | 190 | 600-900 | 0.5 | 0.28 | 142.78 | 100.0 |
| G-69B | 202 | 1200 | 1 | 7.72 | 1 | 82.0 |
| G-69B | 201 | 1200 | 2 | 5.01 | 4.078 | 88.3 |
| G-69B | 198 | 1300 | 3 | 3.04 | 5.323 | 92.9 |
| G-69B | 200 | 1400 | 4 | 1.68 | 6.228 | 96.1 |
| G-69B | 201 | 1400 | 5 | 1.07 | 6.479 | 97.5 |
| G-69B | 220 | 1600 | 5.5 | 0.469 | 6.977 | 98.9 |
| G-49B | 204 | 1200 | 1 | 62.14 | 23.09 | 85.5 |
| G-49B | 202 | 1200 | 2 | 52.89 | 44.68 | 87.6 |
| G-49B | 201 | 1200 | 3 | 26.24 | 39.29 | 93.9 |
| G-49B | 199 | 1000 | 1 | 79.43 | 6.26 | 81.4 |
| G-49B | 200 | 1000 | 2 | 40.73 | 31.94 | 90.5 |
| G-49B | 199 | 1100 | 3 | 24.91 | 37.61 | 94.2 |
| G-49B | 200 | 1000 | 4 | 13.78 | 42.23 | 96.8 |
| G-49B | 200 | 1000 | 6 | 6.4 | 44.9 | 98.5 |
| G-49B | 200 | 1000 | 7 | 2.36 | 47.02 | 99.4 |

It also has been surprisingly discovered, that partial hydrogenation can advantageously be performed using sample mixtures that less pure, for example, mixtures containing residual reagents and products from the reaction of fructose, an acid catalyst and an alcohol that were used to synthesize the starting HMF ether, without further purification. Such crude HMF ether compositions that also are suitable for partial hydrogenation typically contain on a dissolved solids basis, less than 40% or more typically less than 80% of the HMF ether, less than 20% of alkyl levulinate, less than 20% HMF, less than 25% carbohydrates, and trace humins, the later being polymerized bi-products of the ether formation reaction.

While not being bound by theory, it is believed that more highly substituted furfurals such as the HMF ethers and esters used in the present invention, are more difficult to hydrogenate than HMF itself, and that the presence of alkyl levulinates, carbohydrates, salts, and polymers reduces the efficiency of hydrogenation of the furan ring in the HMF ether by occupying the catalytic sites and reacting with a portion of the hydrogen. It is surprising however, that these materials do not interfere with the reduction of the 2' aldehyde to the hydroxyl derivative since the amount of conversion of the HMF ether to the HMF ether furan 2-methanol is nearly quantitative, with at least 60%, and more typically at least 80% of the HMF ether being converted to the partially reduced derivative. In addition, the partial reduction of HMF ethers generally require less time and can occur using lower pressures than needed for the total reduction of HMF ethers. Table 3 below illustrates a summary of exemplary conditions for partially hydrogenation of butoxy methyl furfural to the furan derivative using less purified starting material:

TABLE 3

| catalyst | Starting purity BMF (%) | temp (C.) | pressure (psi) | time (h) | conversion (%) |
|---|---|---|---|---|---|
| 10% G22/2 (Ba CuCr) | 70 | 190 | 600-800 | 0.5 | 97.3 |
| 1% G69B (Ni on Zr) | 15 | 200 | 800-1200 | 3.5 | 99.7 |
| 7% Raney Nickel | 20 | 200 | 1000 | 1 | 99.6 |
| 10% G69B (Ni on Zr) | 20 | 200 | 1300 | 3 | 99.8 |
| 10% G46 (Ni on alumina/silica) | 20 | 200 | 1200 | 2 | 98.7 |
| 10% Pd/C | 20 | 200 | 1000 | 3.5 | 99.6 |
| 3% Pd/C | 20 | 200 | 500 | 2.5 | 99.2 |
| 5% Ru/C | 20 | 200 | 1300 | 2.5 | 99.1 |

While Table 3 above presents summary information Table 4 below, shows actual results from a variety of test conditions with different catalyst for partial hydrogenation of BMF:

TABLE 4

| catalyst | temp C. | pressure (psi) | time (h) | BMF (g/kg) | partially reduced BMF (g/kg) | Conversion (%) |
|---|---|---|---|---|---|---|
| 1% G69B | 200 | 400-1200 | 3.5 | 115.32 | na |  |
| 1% G69B |  |  |  | 0.4 |  | 99.7 |
| 1% G69B | 200 | 1300 | 1.5 | 106.47 | na |  |
| 1% G69B |  |  |  | 0 |  | 100.0 |
| 1% G69B | 200 | 1200 | 4 | 106.47 | na |  |
| 1% G69B |  |  |  | 64.89 |  | 44.3 |

TABLE 4-continued

| catalyst | temp C. | pressure (psi) | time (h) | BMF (g/kg) | partially reduced BMF (g/kg) | Conversion (%) |
|---|---|---|---|---|---|---|
| 10% G22/2 | 190 | 900 | 0.5 | 204 | | |
| 10% G22/2 | | | | 5.9 | 123.43 | 97.3 |
| 30% G96B | 200 | 1300 | 1 | 204 | | |
| 30% G96B | | | | 2.22 | 117.03 | 99.0 |
| 10% G96B | 200 | 1300 | 4 | 204 | | |
| 10% G96B | | | | 0.31 | 6.71 | 99.9 |
| 10% Pd/C | 140 | 550 | 2 | 204 | | |
| 10% Pd/C | | | | 40.69 | 32.67 | 81.6 |
| 10% Raney Ni | 200 | 1000 | 3 | 204 | | |
| 10% Raney Ni | | | | 1.25 | 37.24 | 99.4 |
| 10% G96B | 200 | 1300 | 3 | 204 | | |
| 10% G96B | | | | 0.36 | 49.19 | 99.8 |
| 10% G46 | 200 | 1200 | 2 | 204 | | |
| 10% G46 | | | | 2.84 | 322.88 | 98.7 |
| 10% Pd/C | 200 | 800 | 1.5 | 204 | | |
| 10% Pd/C | | | | 10.13 | 49.95 | 95.4 |
| 10% Pd/C | 200 | 1000 | 3.5 | 204 | | |
| 10% Pd/C | | | | 0.89 | 62.66 | 99.6 |
| 3% Pd/C | | | | 204 | | |
| 3% Pd/C | 200 | 585 | 1 | 25.46 | 53.23 | 88.5 |
| 3% Pd/C | 202 | 580 | 2 | 6.93 | 61.9 | 96.9 |
| 3% Pd/C | 201 | 580 | 2.5 | 1.69 | 57.47 | 99.2 |
| 3% Pd/C | 200 | 400 | 3 | 1.3 | 56.28 | 99.4 |
| 5%Ru/C | | | | 204 | | |
| 5%Ru/C | 199 | 800 | 1.25 | 5.79 | 164.08 | 97.4 |
| 5%Ru/C | 196 | 1100 | 2 | 2.95 | 203.52 | 98.7 |
| 5%Ru/C | 199 | 1300 | 2.5 | 1.94 | 204.94 | 99.1 |
| 5%Ru/C | 202 | 1100 | 3.5 | 2.14 | 165.51 | 99.0 |
| | | | | 204 | | |
| raney Ni | 199 | 1000 | 1 | 0.913 | 7.386 | 99.6 |
| raney Ni | 202 | 800 | 2 | 0.143 | 9.09 | 99.9 |
| raney Ni | 201 | 1200 | 3 | 0.04 | 8.44 | 100.0 |
| raney Ni | 200 | 1200 | 3 | 0.019 | 4.596 | 100.0 |
| G-96B | 200 | 1200 | 0 | 204 | | |
| G-96B | 199 | 1400 | 1 | 63.77 | 30.36 | 70.2 |
| G-96B | 200 | 1400 | 2 | 29.61 | 68.91 | 86.2 |
| G-96B | 201 | 1400 | 3 | 12.97 | 83.84 | 94.0 |
| G-96B | 200 | 1400 | 4 | 3.69 | 83.79 | 98.3 |
| G-96B | 200 | 1400 | 5 | 1.63 | 82.51 | 99.3 |
| raney Ni | 203 | 1400 | 0 | 204 | | |
| raney Ni | 203 | 1400 | 1 | 15.8 | 73.27 | 92.9 |
| raney Ni | 201 | 1400 | 2 | 2.57 | 92.99 | 98.8 |
| raney Ni | 201 | 1400 | 3 | 0.87 | 81.21 | 99.6 |
| raney Ni | 199 | 1400 | 3.5 | 0.76 | 43 | 99.7 |
| raney Ni | 200 | 1400 | 5 | 0.4 | 14.52 | 99.8 |
| 1% G69B | 200 | 1400 | 1.5 | 150 | na | |
| 1% G69B | | | | 54.37 | | 63.8 |

Accordingly, based upon what has been presented herein, one skilled in the art may determine a variety of favorable temperatures, pressures, reaction times and catalyst suitable for both full and partial hydrogenation of a variety of HMF ethers.

Because HMF is made from fructose derived from plant material, one particularly beneficial use of the partial and completely reduced HMF ethers made according to the present invention is as a renewable bio based substitute for solvents typically made from petroleum derived sources, particularly as substitutes for glycol ethers such as carbiotols, which are derived from petrochemical processes. For example, (5' butoxymethyl) tetrahydrofuran can be used as a substitute for butyl carbitol. A comparison of the structures is shown below:

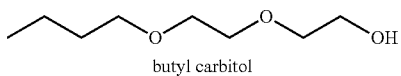

butyl carbitol

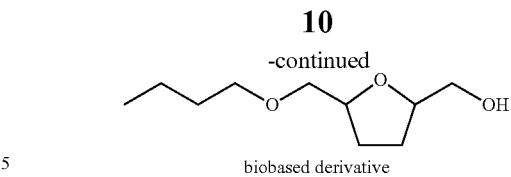

biobased derivative

Another use of the reduced alkoxy furans and tetrahydrofurans made by the methods herein, is as a starting material for further hydrogenation of the ring structure to affect ring opening resulting in a new class of R n-alkoxy hexane diols, which is another aspect of the present disclosure. This ring opening, in combination with the double-bond reducing hydrogenation step produces alkoxy-polyols that are biobased products useful for a wide variety of applications such as solvents, polymers and surfactants. Shown below are the R n-alkoxy hexane 1,2 diol and the R alkoxy hexane 1,5 diols that result from the ring opening reactions:

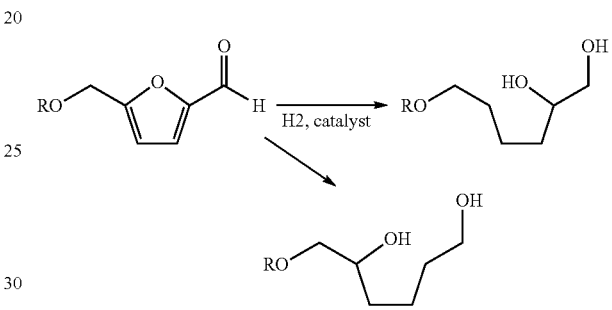

In a one step practice, as depicted above, these n-alkoxy hexanediols can be made by starting with the same catalyst and the same 5'alkoxy furfural compound used to make the partial and complete furan and tetrahydrofuran derivatives, but extending the reaction time, increasing the temperature or increasing the pressure, or increasing the amount of catalyst so that hydrogen is further added to the 2' or 5' carbon atoms to break the ring.

One example reaction condition for this one step practice was use of a Ru/C catalyst at about $\frac{1}{10}^{th}$ the weight of a purified sample of the 5'alkoxy furfural compound, in an ethanol solvent and conducting the reaction at 1200 psi $H_2$ at 170° C. for six hours. In another exemplary practice, still using ethanol as a solvent, the G 69B Ni catalyst with zirconium promoter was used at about $\frac{1}{15}^{th}$ the weight of the purified 5'alkoxy furfural compound, the reaction was conducted at 1200 psi at 200° C. for 5 hours. In both cases, GC/MS analysis showed at least 20% conversion of the 5'alkoxy furfural compound to the n-alkoxy hexanediol son one of ordinary skill in the art will recognize that higher temperatures and pressures, or prolonged times would result in still further production of the n-alkoxy hexanediols. Thorough conversion is expected at any pressure of at least 1000 psi at any temperature of at least 170° C. and the time can be varied as need to be sufficient to make the alkoxy hexane diols without hydrogenating the alcohol groups.

In a better, two step practice, the 5'alkoxy furfural ethers are first completely or partially hydrogenated to form the reduced n-alkoxy furan or tetrahydrofuran derivatives as described herein before, and then these compounds are subsequently purified and hydrogenated under the harsher conditions to produce the n-alkoxy hexanediols. In an exemplary practice, the G 69B Ni catalyst with zirconium promoter was used at about $\frac{1}{15}^{th}$ the weight of the 5'alkoxy furan derivative in a butanol solvent, which was treated at 1200 psi for 200 C for four hours. Under these conditions at least 70% of the partially reduced furan was converted to the n-alkoxy hexane diol derivative. Again, thorough conversion is expected with any pressure of at least 1000 psi at any temperature of at least 170° C. and the time can be varied as need to be sufficient to make the alkoxy hexane diols without hydrogenating the alcohol groups.

The foregoing reaction conditions can also be used for complete and partial reduction of HMF esters having an R-acyloxymethyl group at the 5-position on the HMF ring. The acyl group may be either straight chained or branched, having from 1 to 24 carbon atoms, and may also contain oxygen, nitrogen, or sulfur. More typically, R is an alkyl group of one to 5 carbons. Some preferred acyl groups are including, but not limited to acetic, propionic, butyric, or citric. These partial and completely reduced acyl substituted HMF ester derivatives have the general structures depicted below:

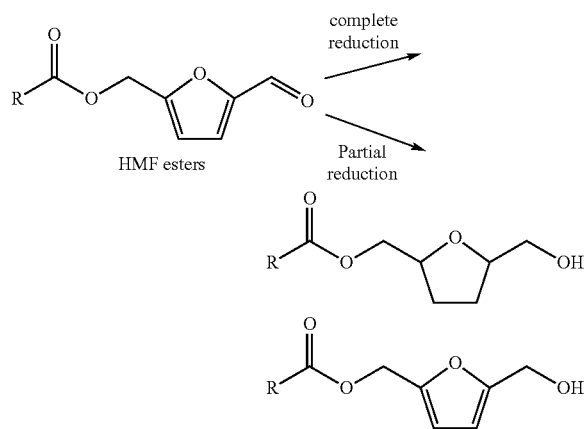

In one exemplary practice, a purified acetoxy HMF ester, where R=2, was reduced to the partially hydrogenated furan derivative by use of 10% wt/wt G-22/2 barium promoted copper chromite catalyst at 190° C., 950 psi, for one hour. These reactions are very similar to those used to make the furan derivatives from the HMF ethers as described in greater detail herein before. It is clear therefore, that any of the similar reaction conditions and catalysts described for the HMF ethers can be applied to the complete or partial reduction of HMF esters as well.

Generally, the reduction of HMF derivatives by the methods described herein are carried out in a reaction vessel capable of withstanding high temperatures and pressures. Typically, reaction vessels comprised of high strength and high durability steel, which are resistant to corrosion and chemical oxidation are preferred. Preferably, the reaction vessel has at least one inlet to allow for addition of hydrogen gas to the reaction mixture before and during the reaction. A pressure gauge to monitor the pressure of the reaction is also preferably attached to the vessel. The reaction vessel is also preferably equipped with a stirrer to allow for sufficient agitation of the reactants during the hydrogen purging and during the reaction, although other known methods for mixing the reaction may be employed, such as use of a magnetic stirrer. One such vessel that may be used in the embodiments in the present disclosure is an Autoclave Engineers (Snap-tite, Inc., Erie, Pa.) high pressure reactor.

Generally, the solvent used in the reactions preferably will dissolve the HMF derivative starting material at least at the temperature at which the reaction occurs. In addition, it is favorable to use a solvent that is easily removed after the reaction by common laboratory methods such as rotary evaporation. Some preferred solvents are methanol, ethanol, n-propanol, i-propanol, n-butanol, i-butanol, acetone, ethyl acetate and the like. More preferably, the solvent is ethanol.

The amount of solvent used preferably will be sufficient to provide for adequate dissolution of the reactants, as well as to allow for the solution to be stirred at a rate sufficient to allow the reactants to mix during the reaction. The use of too little solvent may prevent adequate mixing of reactants. The use of too much solvent may require excessive energy to remove and increases the cost of the reaction, the time to remove the solvent and the cost of disposal of the solvents. Generally, the reaction mixture utilizes an amount of about 1 to 50 wt/vol % starting material in relation to the solvent, preferably, about from 5 to 20 wt/vol % starting material to solvent.

Generally, the temperature at which the reaction occurs determines the rate of conversion of starting material, and amount of side product formation. With the present disclosure, the temperature preferably is high enough to allow for the reactants to interact and be converted into the product, but not too high to cause decomposition of the reactants, products or intermediates. Preferably, the temperature range of the reaction is from about 125° C. to about 250° C. More preferably, the temperature range is from about 170° C. to about 205° C.

Generally, the pressures at which the reactions are run are from between about 500 and about 1500 psi but can be varied with selection of reagents different catalysts, and times. In most embodiments, the pressure is between about 1000 and about 1500 psi.

Generally, the reaction time must be sufficient to allow the reaction to proceed to the desired level of completion without generation of side products. Depending on specific reactants, amounts, purity of reactants, catalyst selection, and pressure, the reaction time can be from 30 minutes to overnight (approximately 15 hours). In others, the reaction time is from 30 minutes to 5 hours; and still others, the reaction time can be from 30 minutes to 3 hours. Based on the present disclosure, those skilled in the art will readily be able to adjust the reaction time and temperature as necessary to maximize the yield of the reaction without undue experimentation.

Any known method for purification of the end products may be used, such as crystallization, distillation, solvent-solvent extraction, column chromatography, carbon treatment, adsorption and the like. One preferred method is fractional distillation under reduced pressure.

While the present disclosure has described in more detail certain particular HMF derivatives that can be made from the reduced HMF esters and ethers made according to the present teaching, there are many other derivatives that one of ordinary skill in the art can make from such compounds. For example, the reduced HMF ethers and esters can be converted into acrylates by conversion of the hydroxide grouped at the $C_1$ position for use as monomers in the synthesis of polymeric derivatives. These HMF acrylates would have pendant furan and tetrahydrofuran substituents. The furan containing monomers may be used for latent cross linking or production of thermosetting thermoplastics.

For another useful derivative, the reduced or partially reduced HMF ethers or esters may undergo reductive amination to produce amine substituted HMF ethers and esters capable of undergoing substitution reactions typical of amines. These compounds are useful for amide synthesis, or undergoing further amination to produce quaternary ammonium salts, which are useful for a variety of applications, such as surfactants or disinfectants. Amine-containing HMF derivatives may also be converted into acrylamide derivatives at the $C_1$ position.

For yet another useful derivative product, the reduced or partially reduced HMF ethers or ester s containing either a hydroxyl or amine functionality may be used to functionalize oxidized (acidic) starch. These functionalized starches may be utilized in a number of ways, for example, as chelating agents for trace metal/precious metal recovery, thermally cross linkable materials, super-adsorbent articles (BioSAPs which alternatives to petroleum based SAP, and can be used as composites and thermoplastic materials and modifiers. An example of a synthetic route, which uses simple acid or base catalysis to produce these types of modified starches, is shown in FIG. 1.

Thus, the reduction of HMF derivatives by either reducing the furan ring, the aldehyde moiety, or both is an important method to obtain useful products. However, the reduction of HMF derivatives has often eluded researchers due to low yields and expensive reactants which combine to make the synthesis of derivatives of these compounds non-cost effective. Prior to the present disclosure, there was no known commercially viable procedure for reducing HMF derivatives.

The description provided above may better be understood by reference to the particular examples that follow.

EXAMPLES

The following examples are offered for purposes of illustration and are not intended to limit the scope of the invention.

Example 1

Complete Reduction of Isoamyl HMF 200 mL of purified 15% isoamyl hydroxymethylfurfural in ethanol and 100 mL isoamyl alcohol was added to a 1 L Autoclave Engineers (Snap-tite. Inc., Erie, Pa.) high pressure reactor. To this was added 3.0 g G-69B catalyst (Sud-Chemie, Louisville, Ky.). The vessel was purged with hydrogen (4×500 psi) while continuously stirring the reaction mixture at 1000 rpm. Then, hydrogen was added to the vessel to 1400 psi, and the reaction mixture was heated to 200° C. for 1 hour. The reaction mixture was then cooled to 40° C. followed by vacuum filtration to remove the catalyst. The filtrate was neutralized to pH 8.3 with potassium carbonate followed by removal of the solvent by rotary evaporation to obtain 37.24 g of a maroon oil. The oil was extracted with hexane and decolorized with carbon. UV and GC/MS indicated complete reduction of the isoamnyl hydroxymethylfurfural starting material to 5-isoamyloxymethyl-2-hydroxymethyl tetrahydrofuran. At this time we didn't have a method of quantitatively analyzing the reaction mixture. The results were simply based on GC/MS, weight yield was 100%.

Example 2

Partial Reduction of Butyl HMF 750 mL of 11% butyl hydroxymethylfurfural in butanol obtained from the crude product of the reaction of fructose and butanol under acidic conditions was added to a 1 L high pressure reactor. The crude mixture contained 11% of the HMF ether, 2 of butyl levulinate, 3% of HMF and 70% butanol. To this was added 7.29 g G-69B nickel on kieselgur catalyst. The reaction was run in the same manner as in Example 1 except the pressure was 1200 psi and reaction time was 4 hours. GC/MS and tlc analysis indicated partial reduction of the butyl HMF to 5-butoxymethyl-2-hydroxymethylfuran. The reaction product was fractionally distilled under reduced pressure (2-5 torr) on an oil bath heated to 150-175° C. to achieve 72% yield of 5-butoxymethyl-2-hydroxymethylfuran.

Example 3

Complete Reduction of Ethyl HMF 25 mL of purified 5-ethoxymethylfurfural in 275 mL ethanol was added to a 1 L high pressure reactor. To this was added 3.09 g G-69B nickel on kieselgur catalyst. The reaction was run in the same manner as in Example 1 except the pressure was 1500 psi and reaction time was 4 hours at 15° C. followed by 9.5 hours at 200° C. MS and NMR analysis indicated complete reduction of the 5-ethoxymethylfurfural to 5-ethoxymethyl-2-hydroxymethyl tetrahydrofuran.

Example 4

Complete Reduction of Ethyl HMF

This example was run under the same conditions as Example 3, except that the reaction time and temperature was 14 hours at 200° C. and pressure was 1350 psi. NMR indicated complete conversion to 5-ethoxymethyl-2-hydroxymethyl tetrahydrofuran.

Example 5

Complete Reduction of Ethyl HMF

This example was run under the same conditions as Example 3, except that the reaction time and temperature was 11.5 hours at 250° C. and pressure was 1150 psi. NMR indicated complete conversion to 5-ethoxymethyl-2-hydroxymethyl tetrahydrofuran, no method of quantification.

As such, Examples 3-5 indicate that reduction of ethyl HMF may be achieved under mild conditions and various temperatures and pressures.

Example 6

Partial Reduction of Butyl HMF

Preparation.

A crude butyl HMF reaction mixture (143 g, 56% butyl HMF, 21% butyl levuliante, and 2% HMF) was placed in a 1 L reactor vessel with butanol (200) mL) and G-69B nickel on kieselgur catalyst (8.0 g) was added. Hydrogenation was performed at 20° C. and 1000 psi for 2 hours. The solution was filtered to remove the catalyst and ethanol removed by rotary evaporation to give 18.83 g of orange liquid. GC/MS data and TLC analysis revealed partial hydrogenation of butyl HMF and 100% conversion of the BMF.

Purification.

A 113.30 g sample of the hydrogenated butyl HMF prepared as describe above was subjected to fractional distillation under reduced pressure (2-3 torr) at an oil bath temperature of 120-165° C. A thick bright yellow oil as fraction 1 (49.98 g) contained mostly the partially reduced butyl HMF with some butyl levulinate. Fraction 2, a pale yellow oil (19.58 g), was pure partially reduced butyl HMF. NMR (δ, 1H); 6.20, (dd, 2.0H); 4.51, (s, 2.0H); 4.37, (s, 2.0H); 3.54, (t, 2.0H); 1.57, (m, 2.0H); 1.38, (m, 2.0H); 0.95, (t, 3.0H) for total 90% yield of partially reduced BMF.

Example 7

Partial Reduction of Butyl HMF

Figure 2:
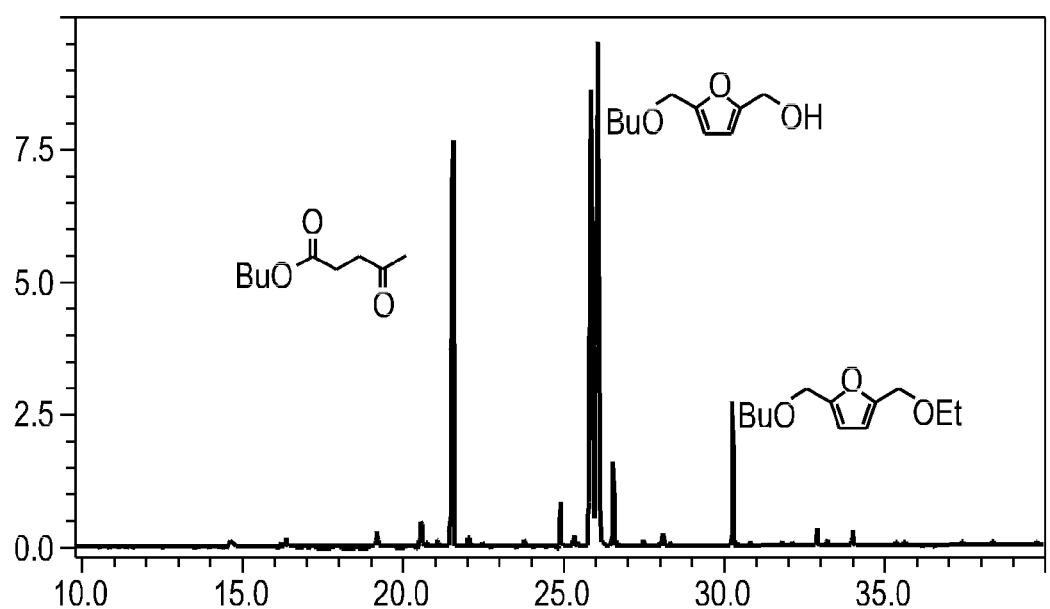
FIG. 2 shows a GC/MA chromatogram of products made in accordance with Example 7.

A crude butyl HMF reaction mixture (11 g, 70% butyl HMF, 3% HMF, 4% butanol, and 18% butyl levulinate) was placed in a 100 mL reactor vessel with ethanol (60 mL) and (G-69B nickel on kieselgur catalyst (0.77 g) was added. Hydrogenation was performed at 150° C. and 600 psi for 1 hour. GC/MS data shown in FIG. 2 and tlc analysis revealed partial hydrogenation of butyl HMF.

Example 8

Partial Reduction of Butyl HMF

A crude butyl HMF reaction mixture (14 g, 70% butyl HMF, 3% HMF, 4% butanol, and 18% butyl levulinate) was placed in a 100 mL reactor vessel with ethanol (50 mL) and G22/2 barium promoted copper chromite catalyst (1.0 g) was added. Hydrogenation was performed at 190° C. and 600-900 psi for ½ hour. The reaction mixture was cooled and the catalyst removed by filtration. A brown liquid (58.4 g) was obtained. GC/MS and $^1$H NMR data and tlc analysis revealed partial hydrogenation of butyl HMF. Rotary evaporation provided 11.5 g of brown oil identified by $^1$H NMR as 80% partially reduced BMF and 20% butyl levulinate for 93% molar yield of partially reduced BMF and 91% molar yield of butyl levulinate.

Example 9

Partial Reduction of Butyl HMF

Figure 3:
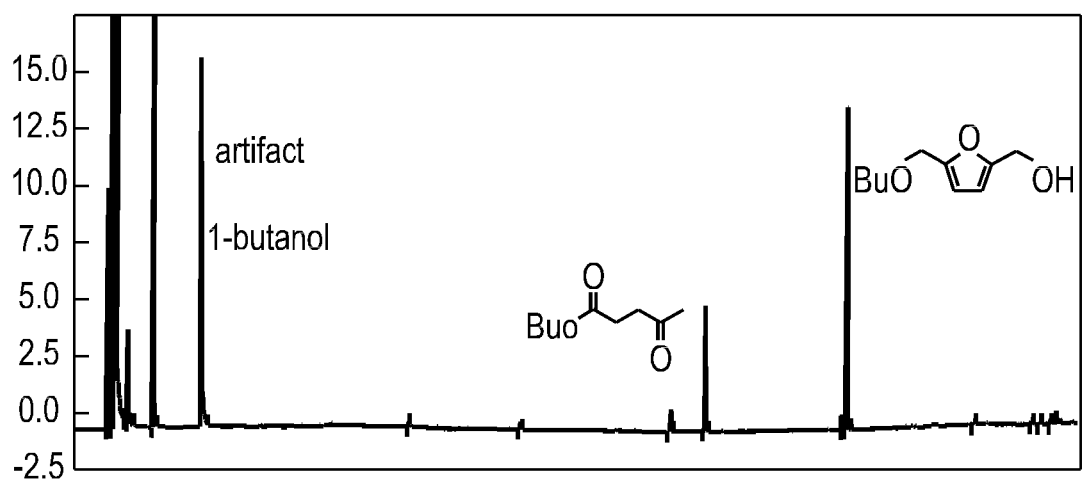
FIG. 3 shows a GC/MA chromatogram of products made in accordance with Example 9.

Preparation.
A crude butyl HMF reaction mixture (64.7 g, 20% butyl HMF, 1.7% HMF, 7% butyl levulinate, and 49% butanol) was placed in a 100 mL reactor vessel with G-22/2 barium promoted copper chromite catalyst (1.3 g). Hydrogenation was performed at 190° C. and 900 psi for ½ hour. The reaction mixture was cooled and the catalyst removed by filtration. A brown liquid (162.5 g) containing 123.43 g/kg partially reduced butyl HMF and 50.03 g/kg butyl levulinate was obtained for quantitative yield. GC/MS shown in FIG. 3 revealed partial hydrogenation of butyl HMF.

Purification.
Approximately 20 g of the hydrogenated butyl HMF described above was subjected to fractional distillation under reduced pressure (9.3 torr) at an oil bath temperature of 150-200° C. Four fractions were collected. $^1$H NMR of fraction 4 (3.2 g, thick yellow oil) indicated substantially pure (>95%) reduced butyl HMF and ~0.4% butyl levulinate.

Example 10

Partial Reduction of Butyl HMF

Figure 4:
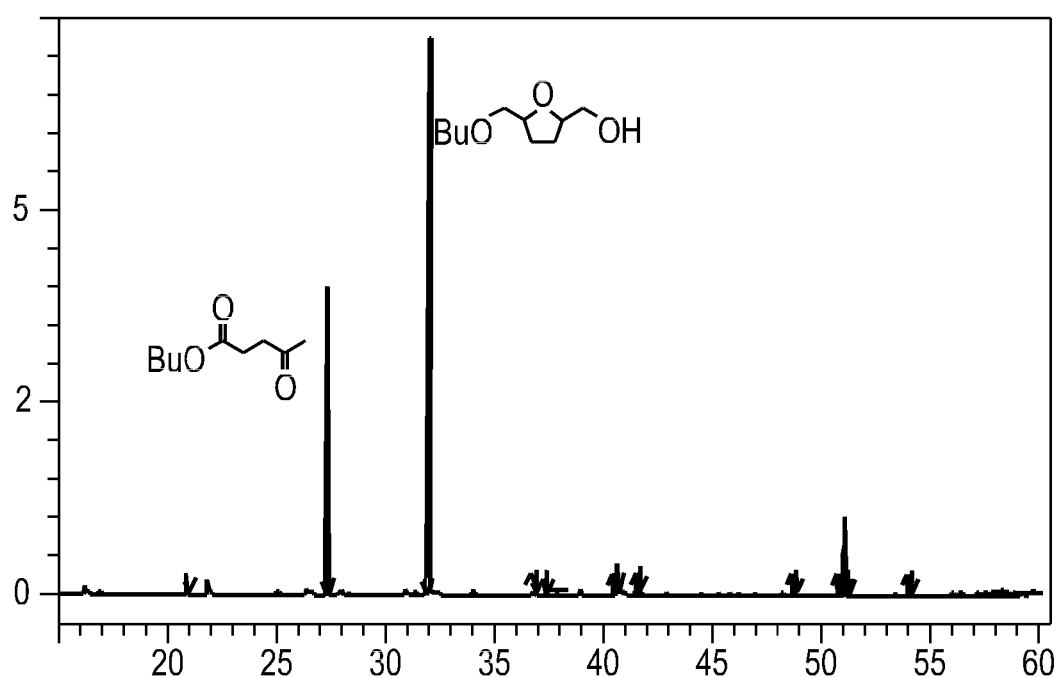
FIG. 4 shows a GC/MA chromatogram of products made in accordance with Example 10.

A crude butyl HMF reaction mixture (54 g, 20% butyl HMF, 1.7% HMF, 7% butyl levulinate, and 49% butanol) was placed in a 100 mL reactor vessel with G-96B nickel on kieselgur catalyst (3 g). Hydrogenation was performed at 200° C. and 1400 psi for 1 hour. The reaction mixture was cooled and the catalyst removed by filtration and washed with butanol. A brown liquid (74.1 g) containing 117.03 g/kg partially reduced butyl HMF (80% molar yield) and 32.07 g/kg butyl levulinate (63% molar yield) was obtained. GC/MS shown in FIG. 4 reveals partial hydrogenation of butyl HMF.

Example 11

Complete Reduction of Butyl HMF

Figure 5:
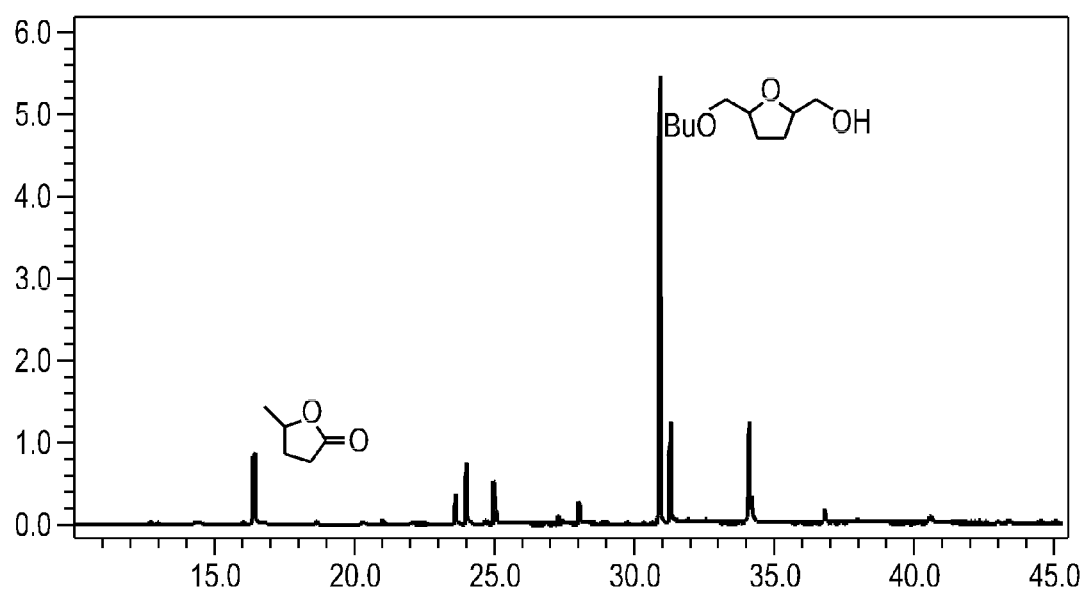
FIG. 5 shows a GC/MA chromatogram of products made in accordance with Example 11.

A crude butyl HMF reaction mixture (25.1 g, 42% butyl HMF, 15% butyl levulinate, 18% HMF) was placed in a 100 mL reactor vessel with Raney Nickel catalyst (1.7 g) and butanol (60 g). Hydrogenation was performed at 200° C. and 1200 psi for 5 hours. The reaction mixture was cooled and the catalyst removed by filtration. An amber liquid (92.8 g) containing 8.32 g/kg completely reduced butyl HMF and 1.02 g/kg butyl levulinate was obtained. GC/MS shown in FIG. 5 reveals complete hydrogenation of butyl HMF at a 90% yield.

Example 12

Complete Reduction of Butyl HMF

Pure butyl HMF (5 g) was placed in a 100 mL reactor vessel with G-69B nickel on kieselgur catalyst (0.25 g) and ethanol (70 mL). Hydrogenation was performed at 170° C. and 1000 psi for 1 hour. GC/MS revealed complete hydrogenation of butyl HMF with 100% conversion of the BMF.

Example 13

Complete Reduction of Butyl HMF

Pure butyl HMF (5 g) was placed in a 100 mL reactor vessel with G-69B nickel on kieselgur catalyst (0.5 g) and ethanol (70 mL). Hydrogenation was performed at 200° C. and 1000 psi for 1 hour. GC/MS revealed complete hydrogenation of butyl HMF.

As can be seen from Examples 6-13, the partial and complete reduction of butyl HMF may be achieved by careful selection of conditions and reactants.

Example 14

Reduction of Crude Butyl HMF 50.0 g of crude butyl HMF (20% BMF, 7% butyl levulinate, 2% HMF, and 49% butanol) was added to the stainless steel reaction vessel along with 20.0 g of 1-butanol; (99.4+% ACS Reagent) and 2.0 g of 10% Pd/C, (Lot #C-3481, $H_2O$=57.67%). The reaction vessel was sealed and stirred for 2 hours at 200° C. with a pressure of 800 PSI and with 610 RPM stirring rate. The reaction was then filtered and the catalyst washed with butanol to provide 74.4 g of filtrate During the reaction, the o-ring was compromised, and the pressure could not be held where it was set. The results indicate concentrations of butyl levulinate at 29.96 g/kg (28% molar yield), butyl HMF at 10.13 g/kg, and partially reduced butyl HMF at 49.95 g/kg for a molar yield of 37% partially reduced product.

Example 15

Reduction of Crude Butyl HMF

The reaction was conducted in the manner described in Example 14 with the following amounts of reactants: 50.1 g of BMF mixture as described in example 14, 20 g of 1-butanol and 2.1 g of 10% Pd/C was sealed and stirred for 3.5 hours at 200° C. with a pressure of 1200 PSI and with 610 RPM. The filtrate (74.2 g) contained butyl levulinate at 30.15 g/kg (28% molar yield), butyl HMF at 0.89 g/kg, and partially reduced butyl HMF at 62.66 g/kg for 46% molar yield.

Example 16

Reduction of Crude Butyl HMF

The reaction was conducted in the manner described in Example 14 with the following amounts of reactants: 54.3 g of butyl HMF (crude) as described in example 14, 20.3 g of 1-butanol: 99.4+% ACS Reagent, 3.0 g of 3% Pd/C, (Süd Chemé) for 3 hours at ~200° C. with a pressure of ~1200 PSI and with ~575 RPM. The results show butyl levulinate at 37.78 g/kg (38% molar yield), butyl HMF at 1.30 g/kg (1% molar yield), and partially reduced butyl HMF at 56.28 g/kg (44% molar yield).

As can be seen in Examples 14-16, the reduction of a crude mixture of HMF ethers to the partially reduced HMF ether may be achieved under the conditions of the present method and by utilization of a crude starting material.

Example 17

Reduction of Crude Butyl HMF

A crude butyl HMF reaction mixture (40 mL, 20% butyl HMF, 1.7% HMF, 7% butyl levulinate, and 49% butanol) was placed in a 100 mL, reactor vessel with G-69B nickel on kieselgur catalyst (0.8 g). Hydrogenation was performed at 200° C. and 1400 psi for 4 hour. The reaction mixture was cooled and the catalyst removed by filtration and washed with butanol. A brown liquid (81.4 g) containing 61.27 g/kg partially reduced butyl HMF (63% molar yield) and 16.5 g/kg butyl levulinate (48% molar yield) was obtained. GC/MS revealed partial hydrogenation of butyl HMF.

Example 18

Reduction of Acetoxymethylfurfural Ester (AcHMF)

Pure acetoxymethylfurfural (AcHMF, 5 g) was placed in a 100 mL reactor vessel with G-22/2 barium promoted copper chromite catalyst (0.5 g) and ethanol (70 mL). Hydrogenation was performed at 190° C. and 950 psi for 1 hour. GC/MS revealed partial hydrogenation of AcHMF.

As is indicated by this experiment, the preparation of the partially reduced form of AcHMF using catalyst and mild reaction conditions may be achieved.

Example 19

Deleted

Example 20

Reduction of Partially Reduced BMF to Butoxyhexane Diol

Figure 6:
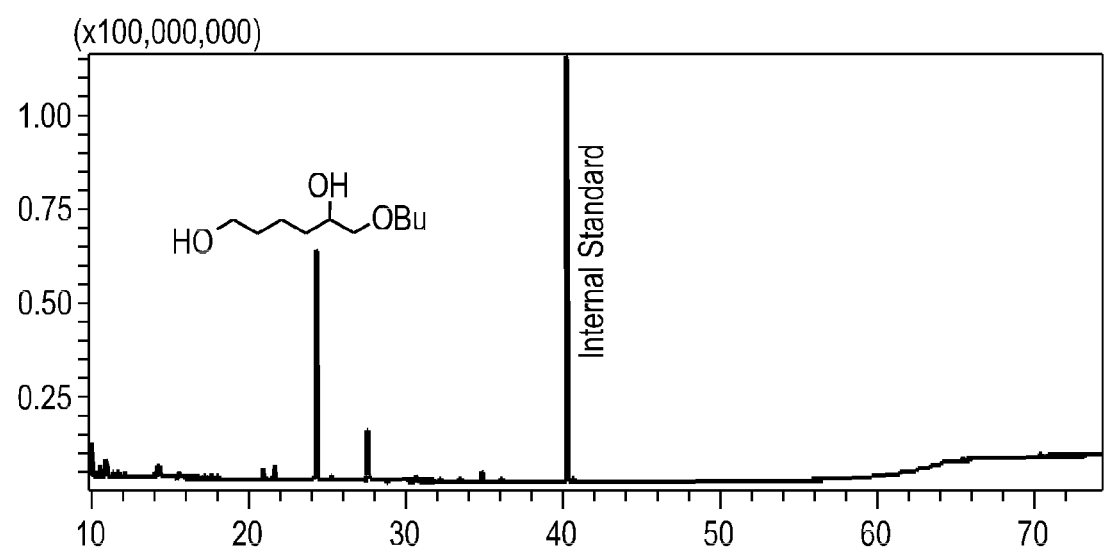
FIG. 6 shows a GC/MA chromatogram of products made in accordance with Example 20.

Crude 5-butoxymethyl-furan-2-methanol (3.1 g, 62%) and 1-butanol (40.0 mL) were placed in a 75 mL high temperature, high pressure Parr reactor. To this reactor was added 0.35 g G 69 B nickel catalyst. The solution was stirred (690 rpm), hydrogen gas added and held at 1200 PSI and heated to 200° C. After four hours, the reactor was cooled and the solution was filtered to remove the catalyst. The catalyst was washed with butanol. The filtrate (59.9 g) was analyzed by GC/MS to show complete conversion of BMF and formation of butoxyhexanediol (FIG. 6).

Example 21

Deleted

Example 22

Reduction of BMF to Butoxyhexane Diol

Butoxymethylfurfural (BMF) (2.0 g, 97% purity) and denatured reagent grade ethanol (40.0 g) were placed in a 75 mL, high temperature, high pressure Parr reactor. To this reactor was added 0.20 g Ru/C (5% Ruthenium) catalyst. The solution was stirred (725 rpm), hydrogen gas added and held at 1200 PSI and heated to 170° C. After six hours, the reactor was cooled and the solution was filtered to remove catalyst. The filtrate (56.6 g) was colorless. Analysis indicated complete conversion of BMF and gc/ms showed the presence of butoxyhexanediol.

Example 23

Reduction of Partiality Reduced BMF to Butoxyhexane Diol

Butoxymethylfurfural (BMF) (3.0 g, 97%) and denatured reagent grade ethanol (40.0 g) were placed in a 75 mL high temperature, high pressure Parr reactor. To this reactor was added 0.20 g G 69B nickel catalyst. The solution was stirred (725 rpm), hydrogen gas added and held at 1200 PSI and heated to 200° C. After five hours, the reactor was cooled and the solution was filtered to remove catalyst. The filtrate (57.1 g) was colorless. Analysis indicated complete conversion of BMF and gc/ms showed formation of butoxyhexanediol.

The foregoing is offered primarily for illustrative purposes. The present disclosure is not limited to the above described embodiments, and various variations and modifications may be possible without departing from the scope of the present invention.

The invention claimed is:

1. A method of making at least one desired compound selected from the group consisting of a (5-acyloxymethyl)-tetrahydrofuran-2-methanol compound of the formula:

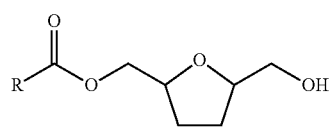

and a (5-acyloxymethyl)-furan-2-methanol compound of the formula:

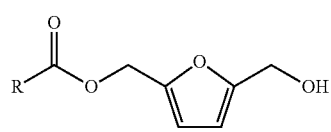

wherein R is an alkyl group of 1 to 5 carbons, comprising contacting a source of R-5'acyloxymethylfurfural ester with hydrogen and a catalyst selected from the group consisting of: a nickel catalyst, a nickel catalyst with a zirconium promoter, a copper chromite catalyst with a barium promoter, a ruthenium catalyst, and a palladium catalyst, at a temperature and a pressure and for a time selected to convert the R-5'acyloxymethylfurfural ester to at least one desired compound in a single step.

2. The method of claim 1, where the source contains at least 40% of the R-5'acyloxymethylfurfural ester as a fraction of dissolved solutes in the source and the desired compound formed is predominantly the (5-acyloxymethyl)-tetrahydrofuran-2-methanol.

3. The method of claim 1, where the source contains at least 40% of the R-5'acyloxymethylfurfural ester as a fraction of dissolved solutes in the source and the desired compound formed is predominantly the (5-acyloxymethyl)-furan-2-methanol.

4. The method of claim 1, where the source contains less than 40% of the R-5'acyloxymethylfurfural ester as a fraction of dissolved solutes in the source and additionally contains at least 20% of a combination of alkyl levulinates and humins as a fraction of dissolved solutes in the source and the desired compound formed is predominantly the (5-acyloxymethyl)-furan-2-methanol.

5. The method of claim 1, wherein the temperature is 140-250° C., the pressure is 500-1500 psi, the time is 30 min to 14 hours, the source is greater than 80% pure, and the reaction converts the acyloxymethylfurfural ester to the (5-acyloxymethyl)-tetrahydrofuran-2-methanol compound.

6. The method of claim 1, wherein the temperature is 170-205° C., the source is less than 80% pure, the pressure is 950-1500 psi, the time is 3-7 hours, the catalyst is Raney nickel, and the reaction converts the acyloxymethylfurfural ester to the 5-(acyloxymethyl)-tetrahydrofuran-2-methanol compound.

7. The method of claim 1, wherein the metal catalyst is on a substrate support.

8. The method of claim 1, wherein the temperature is 140-250° C., the pressure is 500-1500 psi, the time is 30 min to 8 hours, the catalyst is barium promoted copper chromite, and the source is less than 80% pure.

9. The method of claim 1, wherein the metal catalyst comprises nickel with a zirconium promoter on an inert substrate.

10. The method of claim 1, wherein the contacting is in a solvent selected from the group consisting of methanol, ethanol, n-propanol, i-propanol, n-butanol, butanol, acetone, and ethyl acetate, fusel oil alcohols, and any combinations thereof.

* * * * *